United States Patent [19]

Chambron

[11] Patent Number: 4,700,938
[45] Date of Patent: Oct. 20, 1987

[54] EXAMINATION TABLE PROVIDING LINEAR GUIDANCE FOR AN EXAMINATION PANEL

[75] Inventor: Edmond Chambron, Gonesse, France

[73] Assignee: Thomson-CGR, Paris, France

[21] Appl. No.: 841,231

[22] Filed: Mar. 19, 1986

[30] Foreign Application Priority Data

Mar. 22, 1985 [FR] France .................. 85 04336

[51] Int. Cl.$^4$ .............................................. A61G 13/00
[52] U.S. Cl. .................................... 269/322; 378/209
[58] Field of Search ................. 269/322, 73; 378/177, 378/209; 108/137, 143; 384/53, 17

[56] References Cited

U.S. PATENT DOCUMENTS 3,397,411  8/1968  Rossi .................................... 378/209
3,967,126  6/1976  Otto .................................... 378/177
4,475,072 10/1984  Schwehr et al. ..................... 378/209
4,568,071  2/1986  Rice .................................... 108/143

FOREIGN PATENT DOCUMENTS 0077447 10/1981  European Pat. Off. .
2613863  6/1977  Fed. Rep. of Germany ...... 378/209
1378176  9/1963  France .
2403780 11/1977  France .
 675065  5/1950  United Kingdom .

Primary Examiner—Robert C. Watson
Attorney, Agent, or Firm—Oblon, Fisher, Spivak, McClelland, & Maier

[57] ABSTRACT

An examination table for linear guidance of an examination panel in which the panel is guided by means of longitudinal members rigidly fixed to the panel and formed of the same material in order to obtain a small variation in absorption capacity for ionizing radiation.

14 Claims, 4 Drawing Figures

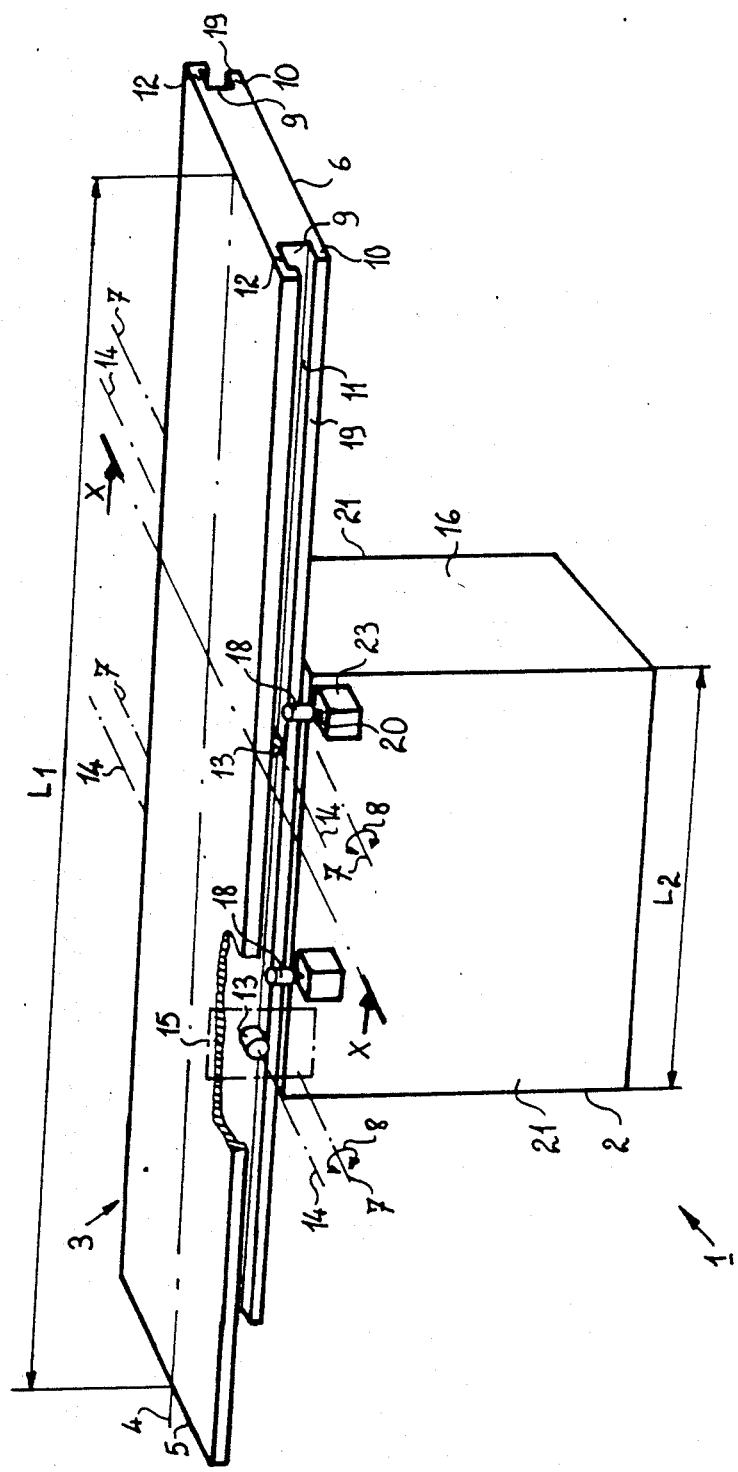

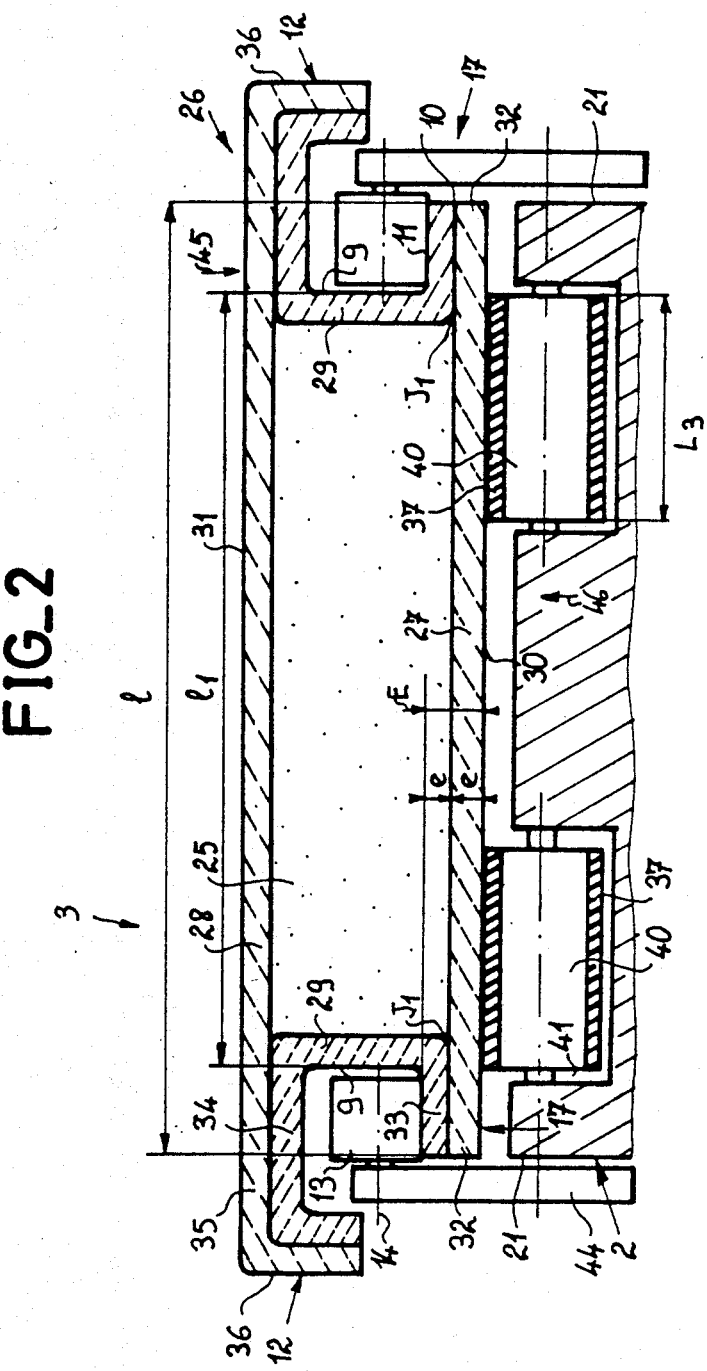
FIG_2

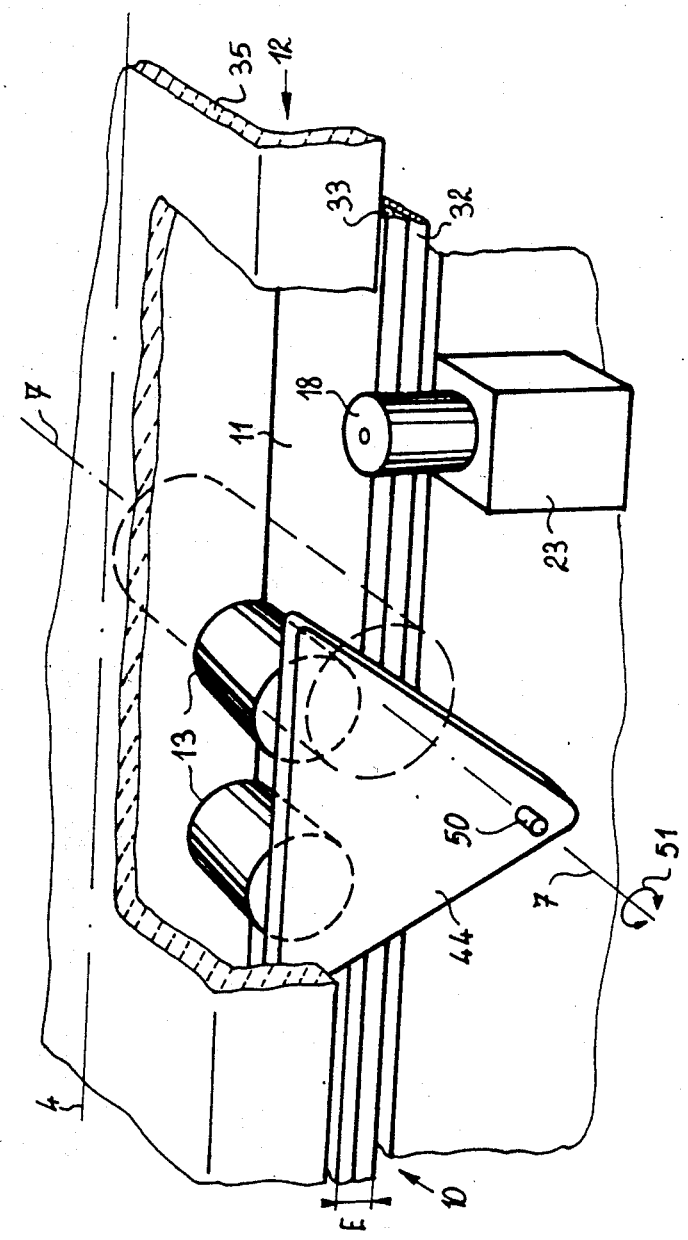

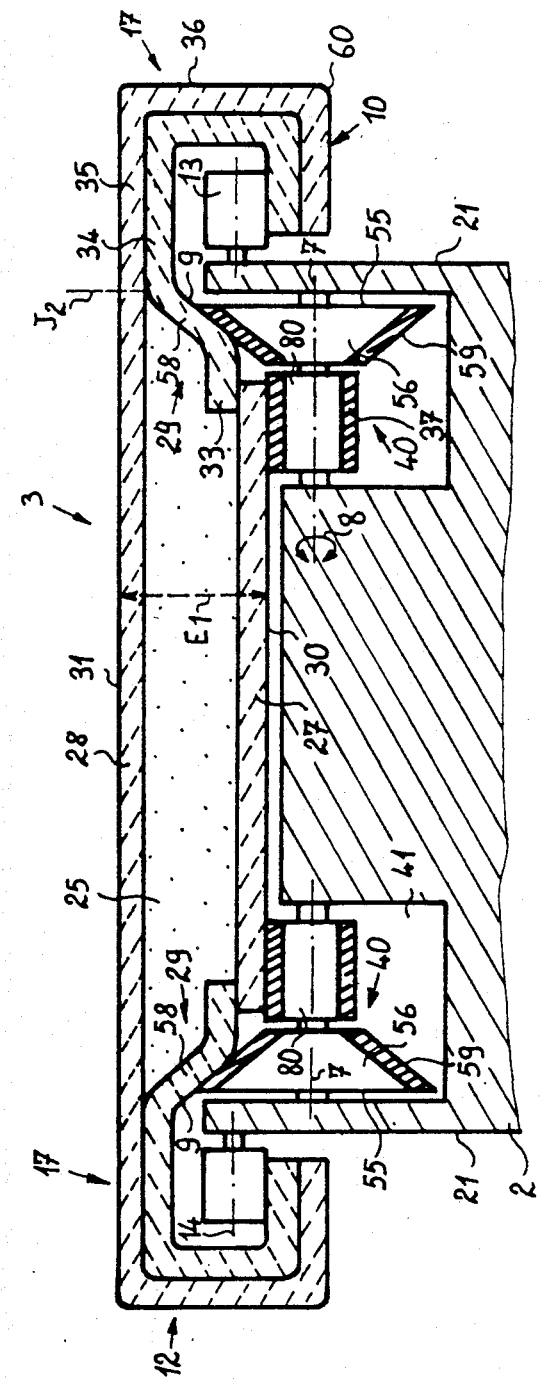
FIG_4

EXAMINATION TABLE PROVIDING LINEAR GUIDANCE FOR AN EXAMINATION PANEL

BACKGROUND OF THE INVENTION

1. Field of the Invention

The present invention relates to an examination table providing linear guidance for an examination panel, potential applications being in the general field of radiology and more specifically in the field of diagnostic radiology.

2. Description of the Prior Art

X-ray scanning of the human body may entail the need to subject a patient to frontal or lateral examinations from head to feet, in which case a longitudinal displacement of the examination panel which supports the patient's body makes it easier to carry out the examinations.

Examination panels proper exhibit a low and homogeneous absorption capacity for ionizing radiation such as x-rays, for example, to which patients are exposed. These conditions are readily retained in the case of frontal examinations.

So far as lateral examinations are concerned, however, and particularly in cases where the axis of the radiation beam is inclined at an angle equal to or smaller than 45° with respect to the plane of the examination panel, a problem which claims attention lies in a discontinuity of absorption of the radiation to which patients are subjected. This discontinuity of absorption is caused by the longitudinal sides of the panel. In the prior art, these longitudinal sides are provided with guiding means which are usually of metal in order to afford high mechanical strength and rigidity for a minimum quantity of material and thus to permit longitudinal displacement and guiding of the examination panel. The radiation absorption capacity of these guiding means, however, is considerably greater than that of the materials which constitute the examination panel.

One improvement consists in providing the sides of the examination panel with guiding means disposed along only one-half the length of the panel. The disadvantage of this arrangement lies in the fact that it limits the range of travel of the examination panel and consequently limits the range of scan of the patient's body in view of the fact that, in addition, the length of the panel is also limited. Apart from cost considerations, this limitation of length of the panel is imposed by its characteristics of mechanical strength and rigidity, particularly when said panel is of a type which has a very low radiation-absorption capacity and when it is mounted in the examination table for displacement over a range of travel such that said panel can be supported in overhung positions.

SUMMARY OF THE INVENTION

This invention relates to an examination table in which an examination panel is guided linearly in a longitudinal displacement and exhibits over its entire length a low and homogeneous absorption capacity for radiation to which a patient is exposed, both in frontal examinations and in lateral examinations. In the present invention, this result is achieved not only by a novel arrangement of the examination panel and of the means for guiding the panel but also by a material which is put to unexpected use in the invention since its composition does not carry out the function for which it was originally intended.

The invention is accordingly directed to an examination table providing linear guidance of an examination panel and comprising a frame with respect to which said examination panel is displaced along a longitudinal axis. There are provided bearing rollers attached to said frame for supporting a bottom face of said examination panel as well as first and second rolling means for guiding said panel. Said examination panel comprises an internal portion formed of a first material and enclosed within an external portion which constitutes a casing and is formed of a second material. Said external portion defines said bottom face, a top face and longitudinal side elements of said examination panel, said side elements being constituted by a longitudinal member which serves to guide said examination panel. The distinctive feature of the invention lies in the fact that the external portion aforesaid comprises at least one projecting portion which extends beyond each longitudinal side element aforesaid and in which said longitudinal member is formed. Said projecting portion is formed in one piece with said external portion in order to be made of the same first material and to retain along said longitudinal side elements a small variation in its absorption capacity for ionizing radiation.

BRIEF DESCRIPTION OF THE DRAWINGS

Other features of the invention will be more apparent upon consideration of the following description and accompanying drawings, wherein:

FIG. 1 is a perspective view showing an examination table in accordance with the invention;

FIG. 2 is a sectional view taken along line X—X of FIG. 1 and showing in greater detail a first embodiment of an examination table in accordance with the invention;

FIG. 3 is a side view showing one example of construction of guiding means;

FIG. 4 is a sectional view taken along line X—X of FIG. 1 and showing a preferred embodiment of the examination table in accordance with the invention.

DETAILED DESCRIPTION OF THE INVENTION

As shown in the perspective view of FIG. 1, an x-ray examination table 1 in accordance with the invention comprises a frame 2 above which is placed an examination panel 3 for receiving a patient (not shown). The examination panel 3 has a longitudinal axis 4 along which said panel is displaced with respect to the frame 2 either by hand or by conventional driving means (not shown) which are placed within the frame 2, for example.

In the non-limitative example herein described, the examination panel 3 has a length L1 which is greater than a length L2 of the frame 2. Depending on the position of the panel with respect to the frame 2, either of the two panel ends (or both ends in the example of FIG. 1) can be mounted in an overhung position. The examination panel 3 is supported on the frame 2 by bearing rollers (not visible in FIG. 1) which are attached to the frame 2 and disposed along axes 7 which are transverse to the longitudinal axis 4. In FIG. 1, said bearing rollers are represented schematically by the transverse axes 7 and are mounted so as to be capable of rotating about these axes in the direction indicated by the arrows 8 during each displacement of the examination panel 3.

The examination panel 3 has longitudinal side elements 9 each provided with a longitudinal guide member 10 having a rolling surface 11. In addition, the longitudinal side elements 9 are provided with a protective trough-shaped section 12 located above the longitudinal guide members 10.

As will be explained in greater detail in a continuation of the description relating to FIG. 2, the longitudinal guide members 10 are made of the same material as one of the materials used to form the examination panel 3. The function of the longitudinal members 10 is to play a contributory role in guiding the examination panel 3 without producing any appreciable discontinuity along the longitudinal side elements 9 of the panel in regard to the absorption capacity of said panel for the ionizing radiation or x-radiation (not shown) to which the patient may be subjected.

The stability of the examination panel 3 in its plane results from a combined action of the aforementioned bearing rollers and of first rolling means constituted by reaction rollers 13 which are applied against the rolling surface 11 of the longitudinal guide members 10. Two reaction rollers 13 are visible in the example of FIG. 1. One of these rollers is shown within a chain-dotted rectangular outline 15 and is made entirely visible by means of an opening formed in the drawing of the trough-shaped section 12. Said rollers 13 extend along second transverse axes 14 and are attached to the frame 2 in a manner which is not shown in FIG. 1 for the sake of enhanced clarity of this figure. Reaction rollers 13 of this type are provided on each longitudinal side element 9, preferably in proximity to the transverse walls 16 of the frame 2. At least one reaction roller 13 is adapted to cooperate with each of the aforementioned bearing rollers in order to guard against tilting of the examination panel 3.

Longitudinal guidance of the examination panel 3 is achieved by means of second rolling means which, in the example of said first embodiment of the invention, consist of rollers 18 which run along while being applied against each longitudinal side face 19 of each longitudinal guide member 10. The rollers 18 are each provided with a shaft 20 which is in turn attached to the longitudinal walls 21 of the frame 2 by means of a conventional fixing member 23. At least two second rollers 18 attached to each lateral wall 21 of the frame 2 are necessary for longitudinal guidance of the examination panel 3.

FIG. 2 shows in cross-section along line X—X of FIG. 1 characteristic elements of the examination table 1 in accordance with the first embodiment of the invention.

The examination panel 3 is mainly composed of two different materials, both of which have a low absorption capacity for x-radiation. The first material forms an internal portion 25 which extends substantially over the entire length L1 (not visible in FIG. 2) of the examination panel 3. Said internal portion 25 is formed of compact plastic foam having a high hardness value and consisting of a methacrylic polyimide foam. The internal portion 25 is sandwiched between two plates of an external portion 26 formed from the second material. In the non-limitative example herein described, said second material is constituted by fabrics of composite materials having a base of carbon fibers pre-impregnated with resin.

In the non-limitative example herein described, the external portion 26 comprises a first plate 27 and a second plate 28 which are substantially parallel, and third plates 29. Said first, second and third plates 27, 28, 29 define respectively a bottom face 30, a top face 31 and the longitudinal side elements 9. In accordance with a distinctive feature of the invention, the longitudinal member 10 which serves to guide the examination panel 3 and possibly also the protective trough-shaped section 12 are obtained by design immediately after construction of the examination panel 3. To this end, the external portion 26 comprises, with respect to each of the longitudinal side elements 9, a projecting portion 17 in which the longitudinal guide member 10 is formed. In the non-limitative example herein described, said projecting portions 17 are formed from the first plate 27, the width 1 of which is greater than a width $l_1$ of the examination panel 3 as considered between the longitudinal side elements 9 of said panel. The first plate 27 is thus provided with a first extension 32 on each longitudinal side element 9. The first and second plates 27, 28 are rigidly assembled together along the longitudinal side elements 9 by means of the third plates 29. In the nonlimitative example herein described, the third plates 29 are rigidly fixed to each of the first and second plates 27, 28 by means of a standard method such as hot-state bonding, for example. To this end, each third plate 29 has a bottom bent-back portion 33 and a top bent-back portion 34, said bent-back portions being parallel to the first and second plates 27, 28 with which they are in contact. In more precise terms, the bottom bent-back portion 33 is rigidly fixed to the first extension 32 of the first plate 27, that is to say on the side nearest the bottom face 30, and the top bent-back portion 34 is joined to a second extension 35 of the second plate 28 which projects beyond the longitudinal side elements 9.

In this configuration, each longitudinal guide member 10 is formed in the direction of its thickness E by the first extension 32 of the first plate 27 and by a first bottom bent-back portion 33 obtained from the third plates 29. The thickness e of said first extensions 32 and the thickness e of said bottom bent-back portions 33 are added. Similarly, the thickness of the second extensions 35 of the second plate 28 is added to the thickness of the top bent-back portions 34 of the third plates 29. The thicknesses just mentioned are not shown in the drawings. The aforesaid second extensions 35 and top portions 34 extend outwards from the examination panel 3 above the longitudinal guide member 10 and are also elbowed so as to be provided with a side-wall element 36 with which they constitute the protective trough-shaped sections 12.

The examination panel 3 is supported by the bearing rollers 40 mentioned earlier. In the non-limitative example of the description, the bearing rollers 40 are partially engaged within housings 41 formed in the frame 2 and are secured to this latter for rotation about transverse axes 14 by conventional means which are not illustrated for the sake of greater clarity of the figure. The bearing rollers 40 have a bearing length L3 on which the bottom surface 30 of the examination panel 3 is at least partially applied. The bearing rollers 40 can also extend along the entire width $l_1$ of the examination panel 3 (in a manner which complies with conventional practice and which is therefore omitted from the drawings).

In accordance with a distinctive feature which is useful for the achievement of enhanced performances of the examination table 1, it is important in this instance as well as in the non-limitative example described to ensure that the bearing length L3 of the bearing rollers 40 supports the examination panel 3 in a zone corresponding to a first junction J1 between the longitudinal side elements 9 and the first plate 27 which forms the bottom surface 30. This arrangement makes it possible to benefit from the greater mechanical strength and rigidity possessed by the examination panel 3 along said longitudinal side elements 9, that is to say by virtue of the third plates 29.

The bearing rollers 40 are provided at their periphery with a flexible portion 37 such as rubber, for example, the function of which is to provide more effective absorption of variations in thickness E of the longitudinal guide member 10. This applies in particular to the case in which each bearing roller 40 cooperates with a single reaction roller 13. As has already been mentioned, the reaction rollers 13 run on tracks 11 constituted in the non-limitative example herein described by the first extension 33 of the side plates 29. The reaction rollers 13 are attached to the frame 2 by means of a yoke 44 and exert on the longitudinal guide members 10 (and consequently on the examination panel 3) a thrust in a direction 45 opposite to the direction 46 of a thrust exerted on the examination panel 3 by the bearing rollers 40. This guards against tilting of the examination panel 3 and has the effect of guiding this latter in its plane.

Any possible variations in thickness E of the longitudinal guide member 10 can be compensated independently of the flexible covering 37 provided on the bearing rollers 40 by making use of two reaction rollers 13 which are adapted to cooperate with each bearing roller 40.

An arrangement of this type is shown in the perspective view of FIG. 3 which corresponds to the portion 15 shown in rectangular outline in FIG. 1. In this view, the protective trough-shaped section 12 has been cut away, with the result that the reaction rollers 13 are no longer concealed. The reaction rollers 13 are attached to the yoke 44 in pairs. Said yoke is in turn attached to the frame 2 by means of a pivot 50 and is capable of rotating about this latter as indicated by the fourth arrow 51. In the non-limitative example herein described, the pivot 51 coincides substantially with the transverse axis 7 on which the bearing roller 40 is fixed, said roller being represented schematically in dashed outline. Since the reaction rollers 13 are applied against the track 11 on which they run as the examination panel 3 is being displaced, the positions of said rollers can follow variations in thickness E of the longitudinal guide member 10 by virtue of the pivotal movement of the yoke 50.

By means of a sectional view taken along line X—X, FIG. 4 illustrates a preferred embodiment of the invention in which the bottom face 30 of the examination panel 3 is applied against the bearing rollers 40 as in the previous example and in which the longitudinal side elements 9 of said panel are also applied against said bearing rollers 40, thus making even more effective use of the mechanical strength and rigidity provided by the third plates 29.

In the non-limitative example herein described, the bearing rollers 40 are constituted by a first portion forming a cylindrical roller 80 and by a second portion forming a conical portion 56. The first portion 80 and the conical portion 56 are located on the same transverse axis 7, on which the conical portion 56 projects with respect to the bottom face 30 of the examination panel 3. An end face 55 of the conical portion 56 which is remote from the first portion 80 (or in other words located at the exterior of the frame 2) constitutes the base of the cone frustum 56. The first portion 80 and the conical portion 56 are mounted in a manner known per se (not shown in the drawings) so as to rotate about a transverse axis 7 in the direction of the arrow 8 and independently of each other since they rotate at different speeds.

The examination panel 3 is thus supported by the bearing rollers 40, not only by its bottom face 30, but also by its longitudinal side elements 9. Said side elements 9 bear on a generator-line 59 of the conical portion 56 and are accordingly made parallel to said generator-line for this purpose.

In the non-limitative example described, the bottom bent-back portions 33 of the third plates 29 are placed in overlapping relation to the first plate 27 and are rigidly fixed to this latter within the examination panel 3. The third plates 29 are so shaped as to have an inclined intermediate portion 58 which is substantially parallel to the generator-line 59 of the cone 56. These inclined intermediate portions 58 constitute the longitudinal side elements 9, extend outwards from the examination panel 3 so as to meet the second plate 28 which forms the top face 31, and are rigidly fixed to said plate 28. Starting from a second junction point J2 represented by a dashed line, the third plate 29 and the second plate 28 extend beyond the longitudinal side elements 9 in order to form the projecting portion 17 along said side elements.

In this exemplified embodiment of the invention, the projecting portion 17 is formed by the second extension 35 of the second plate 28 and by the top bentback portion 34 obtained from the third plate 29. The projecting portion 17 is then downwardly bent in order to form the side-wall element 36 which is substantially parallel to the thickness E1 of the examination panel 3 and thus to obtain the protective trough-shaped section 12 mentioned earlier. In addition, the projecting portion 17 is extended at a lower end 60 of the side-wall element 36 which is elbowed so as to return to the frame 2 and to form a flat portion substantially parallel to the plane of the examination panel 3. This flat portion constitutes the longitudinal guide member 10 on which the reaction rollers 13 travel, with a view to guiding the examination panel 3 in its plane in cooperating relation with the bearing rollers 40.

A point worthy of note in this configuration is that, apart from the fact that the examination panel 3 can thus be supported by its bottom face 30 and by its longitudinal side elements 9, longitudinal guidance of the examination panel 3 is also achieved and the second rollers 18 employed for this purpose in the previous example can thus be dispensed with. In this embodiment of the invention, longitudinal guidance is obtained by means of each longitudinal side element 9 which is applied against the conical portions 56 of the bearing rollers 40. These conical portions 56 thus perform the function of the second rolling means as well as a supporting function for the examination panel 3.

In comparison with an examination table of the same type as used in the prior art, an examination table 1 in accordance with the invention and comprising an examination panel 3 displaceable over a distance L1 with respect to the frame 2 offers in particular the the examination panel 3 is formed over its entire length L1 of materials having a low and homogeneous absorption capacity for ionizing radiations, especially along its longitudinal side elements 9, said side elements being provided with longitudinal guide members 10 made of the same second material as the examination table 1 in order to ensure that homogeneity of radiation absorption along the longitudinal side elements 9 of said table is not impaired; the longitudinal guide members 10 are formed in projecting portions 17 which are integral with the external portion 26 of the examination panel 3; said projecting portions 17 are obtained by design at the time of construction of the examination panel 3 and represent a simplification of assembly and a substantial reduction in cost with respect to the prior art; the arrangement of the examination table 1 in accordance with the invention also makes it possible to increase one range of travel of the examination panel 3 or in other words to provide the second length L2 of the frame 2 with a dimension which is considerably smaller than the length L1 of the examination panel 3 and of the longitudinal guide members 10, particularly by virtue of the fact that the longitudinal side elements 9 themselves are applied against the bearing rollers 40; it is worthy of mention that the arrangement of the examination table 1 in accordance with the invention also makes it possible by design, or in other words at low cost, to provide protective trough sections 12 which may or may not be integral with the longitudinal guide members 10.

What is claimed is:

1. An examination table for linear guidance of an examination panel, comprising a frame with respect to which said examination panel is displaced along a longitudinal axis, bearing rollers attached to said frame for supporting a bottom face of said examination panel, first and second rolling means for guiding said examination panel, said panel comprising an internal portion formed of a first material and enclosed within an external portion which constitutes a casing and is formed of a second material, said external portion being intended to define a bottom face, a top face and logitudinal side elements of said examination panel, said side elements being constituted by a longitudinal member which serves to guide said examination panel, wherein the external portion aforesaid comprises at least one projecting portion which extends beyond each longitudinal side element aforesaid and in which said longitudinal member is formed, said projecting portion being formed in one piece with said external portion in order to be made of the same first material and to retain along said longitudinal side elements a similar absoprtion capacity for ionizing radiation as said examination panel.

2. An examination table according to claim 1, wherein the projecting portion aforesaid is so shaped as to comprise in addition a protective trough section formed in one piece with the longitudinal guide member aforesaid.

3. An examination table according to claim 1, wherein the external portion aforesaid further comprises a second projecting portion formed in one piece with said external portion and extending beyond said longitudinal side elements so as to constitute a protective trough section along each side element opposite to the longitudinal guide member.

4. An examination table according to claim 1, wherein said examination panel has a length L1 greater than a second length L2 of said frame, said examination panel being supported in overhung position along said longitudinal axis.

5. An examination table according to claim 1, wherein the external portion aforesaid comprises a first and a second plate forming respectively said bottom face and said top face, said first and second plates being assembled in rigidly fixed relation by means of third plates forming said longitudinal side elements and wherein junctions between said first and third plates are applied against said bearing rollers.

6. An examination table according to claim 1, wherein said first rolling means are constituted by reaction rollers rigidly fixed to said frame and capable of traveling on said longitudinal guide members, each bearing roller aforesaid being adapted to cooperate with at least one reaction roller which exerts a thrust on said longitudinal guide member in a direction opposite to the direction of a thrust exerted by said bearing rollers on said examination panel in order to ensure stability of said examination panel in its plane.

7. An examination table according to claim 6, wherein each bearing roller is adapted to cooperate with two reaction rollers mounted on a common yoke, said yoke being rigidly fixed to said frame by means of a pivot about which said yoke is capable of carrying out a movement of rotation as a function of a variation in thickness of said longitudinal guide member.

8. An examination table according to claim 1, wherein said longitudinal guide members are provided with external longitudinal side faces which cooperate with second rollers in order to carry out longitudinal guidance of said examination panel, the second rolling means aforesaid being constituted by said second rollers.

9. An examination table according to claim 3 or claim 5, wherein the first projecting portion aforesaid is formed from the first plate by a first extension and from the third plates forming said longitudinal side elements by a bent-back bottom portion being assembled so as to add their thickness (e).

10. An examination table according to claim 5, wherein said second projecting portion is formed from the second plate by a second extension of said plate and from 11. An examination table according to claim 2, wherein said bearing rollers comprise a first portion and a conical portion, said conical portion being so designed as to project with respect to said bottom face and wherein said examination panel is supported on said rollers by the bottom face which is applied against said first portion and by said longitudinal.side elements which are applied against said conical portion, said longitudinal side elements being substantially parallel to a line on the surface of said conical portion.

12. An examination table according to claim 11, wherein the second rolling means aforesaid are constituted by said conical portions, each longitudinal side element aforesaid being adapted to cooperate with said conical portion in order to obtain longitudinal guidance of said examination panel.

13. An examination table according to claim 2 or claim 5, wherein the second projecting portion aforesaid is formed from a second plate forming said top face by a second extension of said plate and from said third plates by a bent-back top portion, said second extension and said bent-back top portion being assembled in such a manner as to add their thickness so as to form said protective trough section and said longitudinal guide member.

14. An examination table according to claim 1, wherein said internal and external portions are formed respectively of a methacrylic polyimide foam and by fabrics of composite materials having a base of carbon fibers preimpregnated with resin.

* * * * *